(12) United States Patent
Okuda et al.

(10) Patent No.: US 10,436,384 B2
(45) Date of Patent: Oct. 8, 2019

(54) BODY FOLLOWING SUPPORT APPARATUS

(71) Applicant: TOHO TECHNOLOGY CORP., Nagoya, Aichi (JP)

(72) Inventors: Hideki Okuda, Kariya (JP); Minoru Takahashi, Kariya (JP)

(73) Assignee: TOHO TECHNOLOGY CORP., Nagoya, Aichi (JP)

( * ) Notice: Subject to any disclaimer, the term of this patent is extended or adjusted under 35 U.S.C. 154(b) by 0 days.

(21) Appl. No.: 15/561,206

(22) PCT Filed: Mar. 28, 2016

(86) PCT No.: PCT/JP2016/059858
§ 371 (c)(1),
(2) Date: Sep. 25, 2017

(87) PCT Pub. No.: WO2016/158837
PCT Pub. Date: Oct. 6, 2016

(65) Prior Publication Data
US 2018/0066794 A1 Mar. 8, 2018

(30) Foreign Application Priority Data
Mar. 27, 2015 (JP) ................. 2015-066722

(51) Int. Cl.
*F16M 13/04* (2006.01)
*A61B 90/60* (2016.01)
*A61B 17/00* (2006.01)
*A61B 90/00* (2016.01)

(52) U.S. Cl.
CPC ............ *F16M 13/04* (2013.01); *A61B 90/60* (2016.02); *A61B 2017/00075* (2013.01); *A61B 2090/064* (2016.02); *A61B 2090/065* (2016.02); *A61B 2090/066* (2016.02)

(58) Field of Classification Search
CPC .... G02B 7/001; G02B 21/0012; A61B 90/25; A61B 90/60; F16M 13/04
USPC ................... 248/280.11, 282.1, 292.11, 550; 414/744.3–744.5; 74/490.01–490.05; 901/15
See application file for complete search history.

(56) References Cited

U.S. PATENT DOCUMENTS

| 5,825,536 A * | 10/1998 | Yasunaga ............... A61B 90/25 359/384 |
| 8,270,073 B2 * | 9/2012 | Nakamura ............. A61B 90/50 359/384 |
| 8,910,913 B2 * | 12/2014 | Hirose ............... A61B 1/00149 248/123.11 |
| 9,375,837 B2 * | 6/2016 | Nakamura ............. B25J 9/1065 |
| 9,841,660 B1 * | 12/2017 | Christensen ......... G03B 17/561 |
| 2006/0263082 A1 * | 11/2006 | Brown ..................... F16F 1/12 396/421 |

(Continued)

FOREIGN PATENT DOCUMENTS

JP  2014018321 A  2/2014

*Primary Examiner* — Muhammad Ijaz
(74) *Attorney, Agent, or Firm* — Harness, Dickey & Pierce, P.L.C.

(57) ABSTRACT

A setting task of a setting unit includes a task to determine, based on a detection result of a detector, whether a click operation is carried out with a part of an operator's body mounted on a mount portion. The click operation is defined as an intentional movement of the part of the body by the operator in accordance with a predetermined pattern.

7 Claims, 4 Drawing Sheets

(56) References Cited

U.S. PATENT DOCUMENTS

| | | | | |
|---|---|---|---|---|
| 2010/0290886 | A1* | 11/2010 | Hashimoto | B25J 9/042 |
| | | | | 414/800 |
| 2013/0041509 | A1* | 2/2013 | Saito | B25J 9/06 |
| | | | | 700/261 |
| 2014/0014804 | A1* | 1/2014 | Okuda | F16M 13/04 |
| | | | | 248/550 |
| 2014/0306086 | A1* | 10/2014 | Okuda | A61B 90/60 |
| | | | | 248/550 |
| 2015/0129741 | A1* | 5/2015 | Okuda | A61B 90/60 |
| | | | | 248/550 |
| 2018/0095234 | A1* | 4/2018 | Nakamura | A61B 90/25 |
| 2018/0168767 | A1* | 6/2018 | Hirose | A61B 90/25 |

* cited by examiner

BODY FOLLOWING SUPPORT APPARATUS

CROSS REFERENCE TO RELATED APPLICATIONS

This application is a U.S. National Phase Application under 35 U.S.C. 371 of International Application No. PCT/JP2016/059858 filed on Mar. 28, 2016 and published in Japanese as WO 2016/158837 A1 on Oct. 6, 2016. This application is based on and claims the benefit of priority from Japanese Patent Application No. 2015-066722 filed on Mar. 27, 2015. The entire disclosures of all of the above applications are incorporated herein by reference.

TECHNICAL FIELD

The present invention relates to body following support apparatuses that support a part of an operator's body and follow motion of the supported part of the operator's body.

BACKGROUND ART

For precise and/or long manual operations, such as neurosurgical operations and the like, there are known body following support apparatuses for supporting a part of an operator's body, such as an arm.

Such a body following support apparatus includes a movable mount member on which a part of an operator's body is mountable.

Specifically, such a body following support apparatus is desired to make the mount member, on which operator's arm is mounted, follow motion of the supported arm, and lock the mount member when the operator wants to fix the supported arm.

In order to meet such desires, there are known technologies, an example of which is disclosed in patent document 1.

The body following support apparatus disclosed in patent document 1 is configured to automatically switch its operation mode between a first operating mode and a second operating mode. The first operating mode is configured to lock movement of the mount member. The second operating mode unlocks the mount member to be freely movable.

In particular, the body following support apparatus disclosed in patent document 1 is configured to automatically switch its operation mode between the first and second operating modes in accordance with a result of comparison between 1. At least one of the level of force applied from the supported arm to the mount member, and the moving speed of the mount member
2. A corresponding at least one of predetermined thresholds

CITATION LIST

Patent Document

[Patent Document 1] Japanese Patent Application Publication No. 2014-18321, which corresponds to US Patent Application Publication No. 2014/014804

SUMMARY

Technical Problem

As described above, the conventional technology applied to the body following support apparatus automatically switches the operation mode of the body following support apparatus between the first and second operating modes in accordance with the result of comparison between 1. At least one of the level of operator's force applied to the mount member, and the operator's moving speed of the mount member
2. A corresponding at least one of the predetermined thresholds The suitable relationships between at least one of the level of operator's force applied by an operator to the mount member and the operator's moving speed of the mount member, and a corresponding at least one of the predetermined thresholds may change depending on operators. For this reason, the conventional body following support apparatus may automatically set its operating mode to unintentional operating mode even if an operator applies force to the mount member to intentionally select the first operating mode or the second selecting mode. An unintentional operating mode set to the conventional body following support apparatus may result in the operator's working efficiency being reduced.

In view of the circumstances set forth above, an exemplary aspect of the present invention seeks to provide body following support apparatuses, each of which is capable of switching its operation mode between a first operating mode to lock movement of the mount member and a second operating mode to unlock the mount member to be freely movable. The exemplary aspect of the present invention seeks to provide such body following support apparatuses, each of which is capable of preventing reduction in the operator's working efficiency due to switching between the first and second operating modes.

Solution to Problem

According to a first exemplary aspect of the present disclosure, there is provided a body following support apparatus (1) for supporting a part of a body of an operator. The apparatus includes a mount portion (5), a support member (3), a brake (31A, 32A, 33A), a balance mechanism (46, 47, 48), a detector (31B, 32B, 33B, 45), and a setting unit (7). A setting task of the setting unit includes a task to determine, based on a detection result of the detector, whether a click operation is carried out with a part of an operator's body mounted on the mount portion. The click operation is defined as an intentional movement of the part of the body by the operator in accordance with a predetermined pattern.

In the body following support apparatus (1) according to the first aspect of the present invention, on the mount portion (5), the part of the body of the operator is mountable. The support member (3) has at least one joint (31, 32, 33, 34, 35), and supports the mount portion to be movable at least vertically by bending of the at least one joint. The brake (31A, 32A, 33A) is configured to achieve 1. A limit state as an operating state of the body following support apparatus, the limit state limiting a function of the at least one joint of the support member to limit movement of the mount portion
2. A release state as the operating state of the body following support apparatus, the release state releasing the limit of the function of the at least one joint to release the limit of the movement of the mount portion The balance mechanism applies upward biasing force to the mount portion in the release state to cause the mount portion to follow movement of the part of the body mounted on the mount portion. For this reason, movement of the part of the body mounted on the mount portion causes the mount portion to follow movement of the part of the body with the operating state of the body following support apparatus being set to the release state.

The detector detects, while the part of the body is mounted on the mount portion, at least one of
  1. Force applied from the part of the body to at least one of the mount portion and the fixing member
  2. Torque applied from the part of the body to the mount portion
  3. An acceleration of the mount portion
  4. A speed of the mount portion
  5. A position of the mount portion
  6. A contact state between the mount portion and the part of the body
  7. A state of the part of the body being close to the mount portion The setting unit performs a setting task to control, based on a detection result of the detector, the brake to set the operating state of the body following support apparatus to any one of the limit state and the release state.

In particular, in the body following support apparatus according to the first aspect of the present invention, the setting task includes a task to determine, based on the detection result of the detector, whether a click operation is carried out with the part of the body. The click operation is defined as an intentional movement of the part of the body by the operator in accordance with a predetermined pattern.

For example, the click operation is defined as an operator's operation to press the mount portion in a predetermined direction other than the upward direction with the part of the body by the operator, and stop the pressing immediately after the pressing. In this example, a parameter and/or a threshold for determining whether the mount portion is pressed associated with determination of whether the click operation is carried out is determined appropriately based on the part of the body of the mount portion and/or how work using the body following support apparatus is being performed. Similarly, the time defining the range of "immediately after" is determined appropriately based on the part of the body of the mount portion and/or how work using the body following support apparatus is being performed.

Such a click operation indicates an operator's intentional operation to set the operating state of the body following support apparatus. For this reason, the body following support apparatus (1) according to the first aspect of the present invention enables an operator's click operation to intentionally switch the operating state of the body following support apparatus. This reduces the operator's distraction.

Note that, as a structure enabling the operator to intentionally switch the operating state of the body following support apparatus, a structure to detect the operator's depression of a pedal with his or her foot can be used if the part of the body mounted on the mount portion is an arm.

Preferably, the click operation can be carried out with the part of the body mounted on the mount portion. This enables the operator to apply his or her mind to the operation of the part of the body, further reducing the operator's distraction.

According to a second exemplary aspect of the present disclosure, there is provided a body following support apparatus (1) for supporting a part of a body of an operator. The apparatus includes a mount portion (5), a support member (3), a brake (31A, 32A, 33A), a balance mechanism (46, 47, 48), a detector (31B, 32B, 33B, 45), and a setting unit (7).

The limit state includes a hold state corresponding to a state in which the part of the body is mounted, and a wait state corresponding to a state in which the part of the body is not mounted.

The setting unit is configured to perform, based on a detection result of the detector, at least one of
  1. A first switching task to switch the operating state of the body following support apparatus from the release state to the hold state
  2. A second switching task to switch the operating state of the body following support apparatus from the hold state to the release state
  3. A third switching task to switch the operating state of the body following support apparatus from the wait state to the hold state
  4. A fourth switching task to switch the operating state of the body following support apparatus from the hold state to the wait state
  5. A fifth switching task to switch the operating state of the body following support apparatus from the release state to the wait state.

The setting unit is also configured to prevent the operating state of the body following support apparatus from being directly switched from the wait state to the release state.

In this case, the support member has at least one joint (31, 32, 33, 34, 35), and supports the mount portion to be movable at least vertically by bending of the at least one joint. The brake is configured to achieve
  1. A limit state as an operating state of the body following support apparatus, the limit state limiting a function of the at least one joint of the support member to limit movement of the mount portion
  2. A release state as the operating state of the body following support apparatus, the release state releasing the limit of the function of the at least one joint to release the limit of the movement of the mount portion The balance mechanism applies upward biasing force to the mount portion in the release state to cause the mount portion to follow movement of the part of the body mounted on the mount portion. For this reason, movement of the part of the body mounted on the mount portion causes the mount portion to follow movement of the part of the body with the operating state of the body following support apparatus being set to the release state.

The detector detects, while the part of the body is mounted on the mount portion, at least one of
  1. Force applied from the part of the body to at least one of the mount portion and the fixing member
  2. Torque applied from the part of the body to the mount portion
  3. An acceleration of the mount portion
  4. A speed of the mount portion
  5. A position of the mount portion
  6. A contact state between the mount portion and the part of the body
  7. A state of the part of the body being close to the mount portion The setting unit performs a setting task to control, based on a detection result of the detector, the brake to set the operating state of the body following support apparatus to any one of the limit state and the release state.

The limit state includes a hold state corresponding to a state in which the part of the body is mounted on the mount portion, and a wait state corresponding to a state in which the part of the body is not mounted on the mount portion.

The setting unit is configured to perform, based on a detection result of the detector, at least one of 1. A first switching task to switch the operating state of the body following support apparatus from the release state to the hold state 2. A second switching task to switch the operating state of the body following support apparatus from the hold state to the release state 3. A third switching task to switch the operating state of the body following support apparatus from the wait state to the hold state 4. A fourth switching task to switch the operating state of the body following support apparatus from the hold state to the wait state 5. A fifth switching task to switch the operating state of the body following support apparatus from the release state to the wait state.

The setting unit is configured to prevent the operating state of the body following support apparatus from being directly switched from the wait state to the release state.

As described above, the hold state is set to correspond to a state in which the part of the body is mounted on the mount portion, and the wait state set to correspond to a state in which the part of the body is not mounted on the mount portion. For this reason, if the operating state were automatically switched from the wait state, which corresponds to a state where the part of the body is separated from the mount portion, to the release state where the mount portion on which the part of the operator's body is mounted is movable to follow movement of the part of the body, the operator would have an anxious feeling.

From this viewpoint, the setting unit according to the second exemplary aspect of the present invention prevents direct switching of the operating state from the wait state to the release state. Additionally, the setting unit performs at least one of the other switching tasks associated with the operating state, such as the switching task to switch the operating state from the release state to the hold state.

This configuration therefore prevents the operating state of the body following support apparatus from automatically switching from the wait state to the release state against the operator's intention, thus reducing the operator's anxious feeling.

Note that reference numerals in parentheses attached to corresponding elements described in this "Solution to Problem" and "Claims" described later are used to merely represent an example of the correspondence relationship between the elements and specific components described in the "Description of Embodiment" described later, and therefore they do not limit the technical scope of the present invention.

DESCRIPTION OF EMBODIMENT

The following describes embodiments of the present disclosure with reference to the accompanying drawings. In each of the following embodiments, there is described a body following support apparatus for supporting an arm, in particular, the forearm of a dominant arm, of a doctor as an example of an operator, who performs surgical operations. However, body following support apparatuses according to the present invention can be designed to support a part of the body of an operator who performs precise and/or long operations during a process of, for example, manufacturing a machine, such as a precision machine. As a part of the body of an operator in addition to an arm, a hand, one or more fingers, a leg, a chin, or the like can be supported by the body following support apparatuses.

1. First Embodiment 1-1 Configuration

Figure 1:
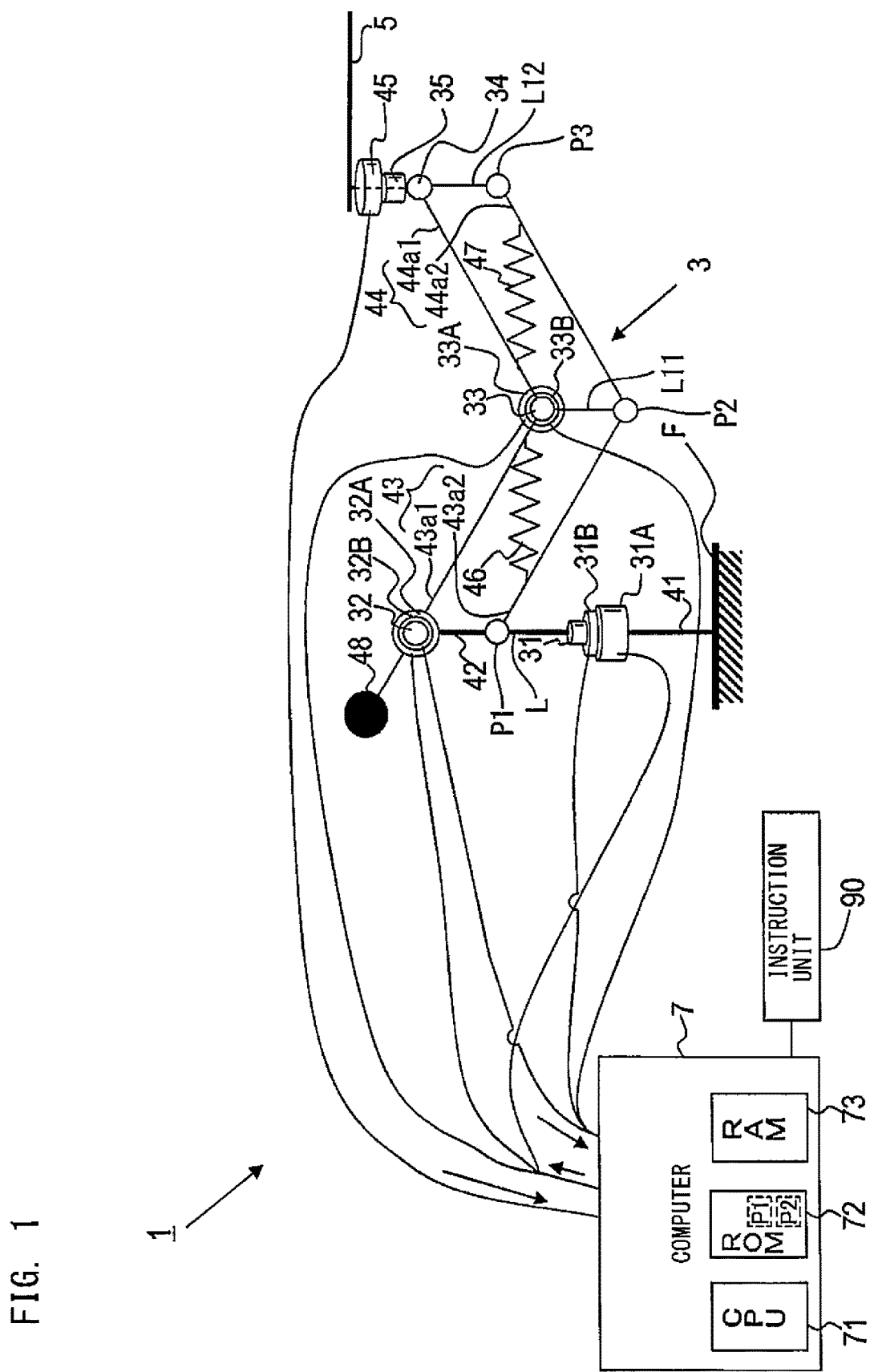
FIG. 1 is a schematic view of a body following support apparatus according to the first embodiment to which the present invention is applied.

As schematically illustrated in FIG. 1, a body following support apparatus 1, to which the present invention is applied, is equipped with a multijoint arm 3, an arm holder 5 attached to a movable end of the multijoint arm 3, and a computer 7 for controlling the multijoint arm 3 and the arm holder 5.

The multijoint arm 3 is designed as a movement mechanism that movably supports the arm holder 5 according to external force applied to the arm holder 5. For example, the multijoint arm 3 has five rotational joints 31, 32, 33, 34, and 35 that provide five degrees of freedom. Note that each of the joints 31 to 35 is configured as a rotational joint.

The multijoint arm 3 includes a base portion 41 and arm body 3A. The base portion 41 has a lower end located on a floor F of an operating room, and has an upper end extending vertically relative to the floor FL. The arm body 3A is supported by the base portion 41.

The arm body 3A includes a shoulder portion 42, a first arm portion 43, and a second arm portion 44 in addition to the joints 31 to 35.

Specifically, the joint 31 is mounted on the upper end of the base portion 41, and the rotational axis of the joint 31 is perpendicular to the floor F.

On the joint 31, a first end of a link L is mounted. On the second end of the link L opposite to the first end, a shoulder portion 42 is mounted to extend upwardly from the second end of the link L. The shoulder portion 42 and the link L are rotatable about the vertical axis of the joint 31. Note that the base portion 41 is equipped with unillustrated casters, so that the base portion 41 is easily movable on the floor F. The base portion 41 also has a known stopper provided for each of the casters. This makes it possible to fixedly locate the base portion 41 at a desired position of the floor F.

To the joint 31, a brake, such as an electromagnetic brake, 31A is attached for reducing rotation of the shoulder portion 42 relative to the supporting base 41. To the joint 31, an encoder 31B is attached for measuring an amount of rotation of the shoulder portion 42 relative to the supporting base 41.

To an upper end of the shoulder portion 42, a joint 32 is mounted such that the rotational axis of the joint 32 is perpendicular to the rotational axis of the joint 31. The first arm member 43 has a first end and a second end opposite thereto. The first end of the first arm member 43 is attached to the joint 32 and the shoulder portion 42 such that the first arm member 43 is swingable about the rotational axis of the joint 32.

For example, the first arm member 43 is designed as a parallel link mechanism comprised of a set of first and second links 43a1 and 43a2. The first and second links 43a1 and 43a2 are configured to move while keeping the first and second links 43a1 and 43a2 in parallel to each other with a constant space therebetween. A first end of the first link 43a1 located over the second link 43a2 is joined to the joint 32. A first end of the second link 43a2 located below the first link 43a1 is also joined to a pivot point P1 to be swingable about a rotational axis of the pivot point P1. The rotational axis of the pivot pin P1 is parallel to the rotational axis of the joint 32, and the pivot point P1 is attached to the second end of the link L.

The second end of the first link 43a1, which is opposite to the first end thereof, is joined to the joint 33 to be swingable about the rotational axis of the joint 33; the rotational axis of the joint 33 extends horizontally. The second end of the second link 43a2, which is opposite to the first end thereof, is joined to a pivot point P2 to be swingable about a horizontal axis of the pivot point P2. The rotational axis of the pivot point P2 extends horizontally. A link L11 connecting between the joint 33 and the pivot P2 is provided. The shoulder portion 42 and the link L11 permit the parallel link mechanism of the first arm member 43 to move while maintaining a constant space between the shoulder portion 42 and the link L11.

The second arm member 44 has a first end and a second end opposite thereto. The first end of the second arm member 44 is attached to the joint 33 such that the second arm member 44 is swingable about the rotational axis of the joint 33.

For example, the second arm member 44 is designed as a parallel link mechanism comprised of a set of first and second links 44a1 and 44a2 configured to move while keeping the first and second links 44a1 and 44a2 in parallel to each other with a constant space between the first and second links 44a1 and 44a2. A first end of the first link 44a1 located above the second link 44a2 is joined to the joint 33, and a first end of the second link 44a2 located below the first link 44a1 is joined to the pivot point P2 to be swingable about a rotational axis of the pivot point P2.

The second end of the first link 44a1, which is opposite to the first end thereof, is joined to the joint 34 to be swingable about the rotational axis of the joint 34; the rotational axis extends horizontally. The second end of the second link 44a2, which is opposite to the first end thereof, is joined to a pivot point P3 to be swingable about a rotational axis of the pivot point P3; the rotational axis of the pivot point P3 extends horizontally.

There is a link L12 connecting between the joint 34 and the pivot P3. The links L11 and L12 permit the parallel link mechanism of the second arm member 44 to move while maintaining a constant space between the links L11 and L12.

To the joint 34, an arm holder 5 is attached via the joint 35 such that a rotational axis of the joint 35 extends vertically to be perpendicular to the horizontally extending rotational axis of the joint 34. To a connection portion between the arm holder 5 and the joint 35, a force sensor 45 is attached; the force sensor 5 is communicably connected to the computer 7.

The force sensor 45 is operative to measure, as a force measurement signal indicative of force applied to the arm holder 5, at least one of first force, second force, and third force respectively applied to the arm holder 5 in a first axis, a second axis, and a third axis. The first, second, and third axes are defined at, for example, a predetermined point of the arm holder 5 through which an extending line of the rotational axis of the joint 35 passes.

The force sensor 45 is also operative to measure, as a torque measurement signal indicative of torque applied to the arm holder 5, at least one of first torque about the first axis, second torque about the second axis, and third torque about the third axis.

The force sensor 45 is further operative to output the measured force measurement signal and torque measurement signal to the computer 7.

Like the joint 31, to the joint 32, a brake, such as an electromagnetic brake, 32A is attached for reducing rotation of the first arm member 43 relative to the shoulder portion 42 around the rotational axis of the joint 32. To the joint 32, an encoder 32B is attached for measuring an amount of rotation of the first arm member 43 relative to the shoulder portion 42.

Additionally, a brake, such as an electromagnetic brake, 33A is attached to the joint 33 for reducing rotation of the second arm member 44 relative to the joint 33 around the rotational axis of the joint 33. An encoder 33B is attached to the joint 33 for measuring an amount of rotation of the second arm member 44 relative to the joint 33.

Each of the brakes 31A to 33A is communicably connected to the computer 7, and can be controlled by the computer 7.

Each of the encoders 31B to 33B is communicably connected to the computer 7, and operative to output the measured amount of rotation to the computer 7.

Between the second link 43a2 of the first arm member 43 and the joint 33, a spring 46 is provided, and, between the second link 44a2 of the second arm member 44 and the joint 33, a spring 47 is provided. The first end of the first link 43a1 of the first arm member 43 extends through the joint 31 to be far from the joint 32 by a preset length. To the extending end of the first link 43a1 of the first arm member 43, counterweights 48 are attached.

The springs 46 and 47 and the counterweights 48 are operative to, when a doctor's arm is mounted on the arm holder 5, apply counterbalancing force to the arm holder 5; the counterbalancing force balances force applied to the arm holder 5 and the multijoint arm 3 caused by the mount of the doctor's arm on the arm holder 5.

Specifically, biasing force from the springs 46 and 47 and the counterweights 48 biases the arm holder 5 upward. The biasing force applied to the arm holder 5 counterbalances the sum of: the weight of the arm holder 5; the weight of a doctor's arm held by the arm holder 5; and the weight of the multijoint arm 3. The sum of these weights will be referred to as an arm total weight hereinafter.

This balance supports the doctor's arm mounted on the arm holder 5.

Note that the biasing force should be ideally counterbalanced to the arm total weight. However, the doctor's arm normally performs surgical operations to an affected site of a patient from above. Thus, in consideration of this matter, the biasing force is determined to bias, with very weak force, the arm holder 5 in the upward direction. This biasing presses the arm holder 5 to be abutted on the arm from below, resulting in frictional force between the arm and the arm holder 5 causing the arm holder 5 to follow the arm.

Figure 2:
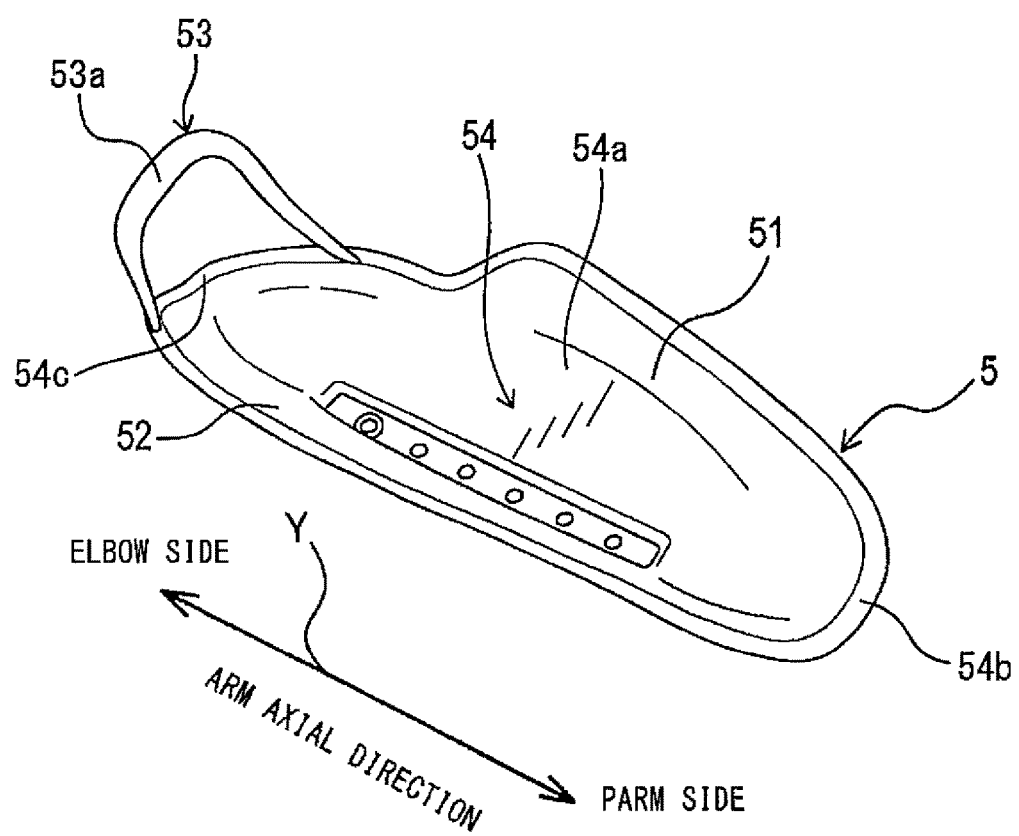
FIG. 2 is a schematic view illustrating an example of the structure of an arm holder of the body following support apparatus illustrated in FIG. 1.

Next, referring to FIG. 2, the arm holder 5 has a substantially longitudinal ellipsoidal base 54 with a top surface 54a on which the forearm of the dominant arm of a doctor is mountable; the top surface 54a will be referred to as a mount surface 54a. The base 54 has a predetermined lateral width.

The arm holder 5 also has a pair of sidewalls 51 and 52 extending upwardly from longitudinal sides of the base 54, so that the arm holder 5 has an opening top and a substantially U-shape in its lateral cross section. The sidewalls 51 and 52 serve to support the doctor's forearm mounted on the mount surface 54a of the base 54 from respective sides of the forearm.

The base 54 has a first end 54b in its longitudinal direction, which is indicated by arrow Y, and a second end 54c opposite to the first end 54b, so that the doctor's forearm is mountable while the elbow is located on the second end 54c of the mount surface 54a of the base 54. Note that the longitudinal direction of the base 54 corresponds to the longitudinal direction of the forearm mounted on the base 54, so that the longitudinal direction of the base 54 will also be referred to as an arm axial direction.

The arm holder 5 includes an elbow-position limiter 53. The elbow-position limiter 53 includes an arched portion, i.e. a substantially U-shaped portion, 53a. Both ends of the U-shaped portion 53a are attached to the base 54 across the second end 54c such that the U-shaped portion 53a is located above the second end 54c of the base 54, so that the U-shaped portion 53a serves as a holder in which a part of the elbow is fittable.

The first end 54b of the arm holder 5 in the arm axial direction is opened to allow the forearm to be easily mounted on the mount surface 54b. The left and right sidewalls 51 and 52 and the elbow-position limiter 53 are each made of, for example, a high-rigidity member. The left and right sidewalls 51 and 52 limit the forearm mounted on the arm holder 54 from moving relative to the arm holder 54. Specifically, the left and right sidewalls 51 and 52 limit the forearm mounted on the arm holder 54 from moving outwardly away from the base 54 in the lateral direction of the base 54. The left and right sidewalls 51 and 52 also limit the forearm mounted on the arm holder 54 from moving toward the second end 54c.

The left and right sidewalls 51 and 52 and the elbow-position limiter 53 can be respectively made of different materials.

Referring to FIG. 1, the computer 7 serves as a state setter that switchably set the operating state of the body following support apparatus 1. For example, the computer 7 integrates therein an electronic control circuit equipped with a CPU 71, a ROM 72, and 1 RAM 73. To the computer 7, the measurement signals sent from the encoders 31B, 32B, and 33B and the force sensor 45 are input.

The CPU 71 of the computer 7 sets, based on the measurement signals, the operating state, i.e. the operating mode, of the body following support apparatus 1 to one of 1. A wait state, i.e. a wait mode
2. A hold state, i.e. a hold mode
3. A free state, i.e. a free mode Then, the CPU 71 controls the operations of the brakes 31A, 32A, and 33A in accordance with the selected operating mode.

The wait state is an operating state, i.e. an operating mode, of the body following support apparatus 1 in which a doctor's forearm is not mounted on the arm holder 5.

The hold state is an operating state, i.e. an operating mode, of the body following support apparatus 1 in which a doctor holds the position of the arm holder 5, and performs a surgical operation using the forearm mounted on the arm holder 5.

The free state is an operating state, i.e. an operating mode, of the body following support apparatus 1 in which the doctor makes the arm holder 5 follow movement of the arm mounted on the arm holder 5.

Referring to FIG. 1, the body following support apparatus 1 also includes an instruction device 90 communicably connected to the computer 7; the instruction device 90 enables various items of information to be instructed or input to the computer 7. The instruction device 90 for example has buttons and/or switches, which are on-off operable by a doctor. The instruction device 90 can be designed as an individual device, such as a foot switch, or as switches and/or buttons mounted on the arm holder 5 and operable by a doctor.

In particular, the instruction device 90 according to the first embodiment is capable of inputting, to the computer 7, an instruction when operated by a doctor; the instruction is to forcibly set the operating state of the body following support apparatus 1 to a lock state, i.e. a lock mode.

The lock state is an operating state, i.e. an operating mode, of the body following support apparatus 1 in which all the brakes 31A, 32A, and 33A are turned on or maintained on independently of any force being applied to the arm holder 5.

[1-2 Operation]

Figure 3:
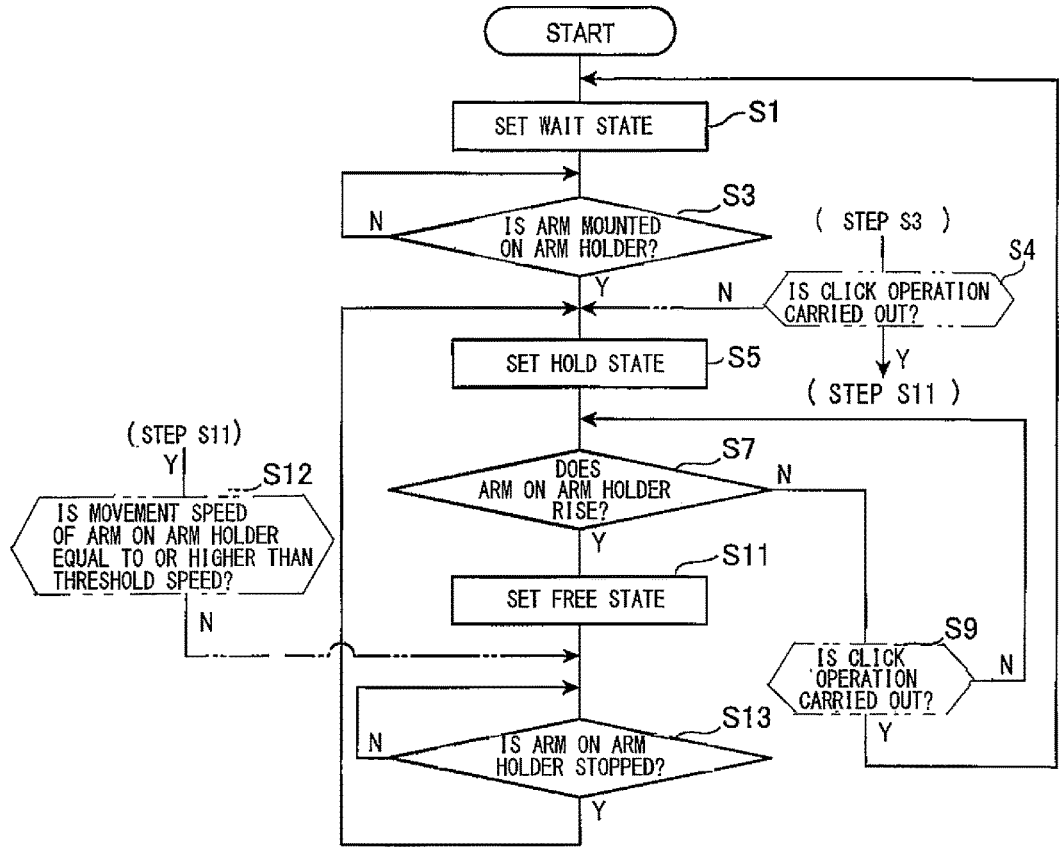
FIG. 3 is a flowchart schematically illustrating a state setting task in the body following support apparatus illustrated in FIG. 1.
Figure 4:
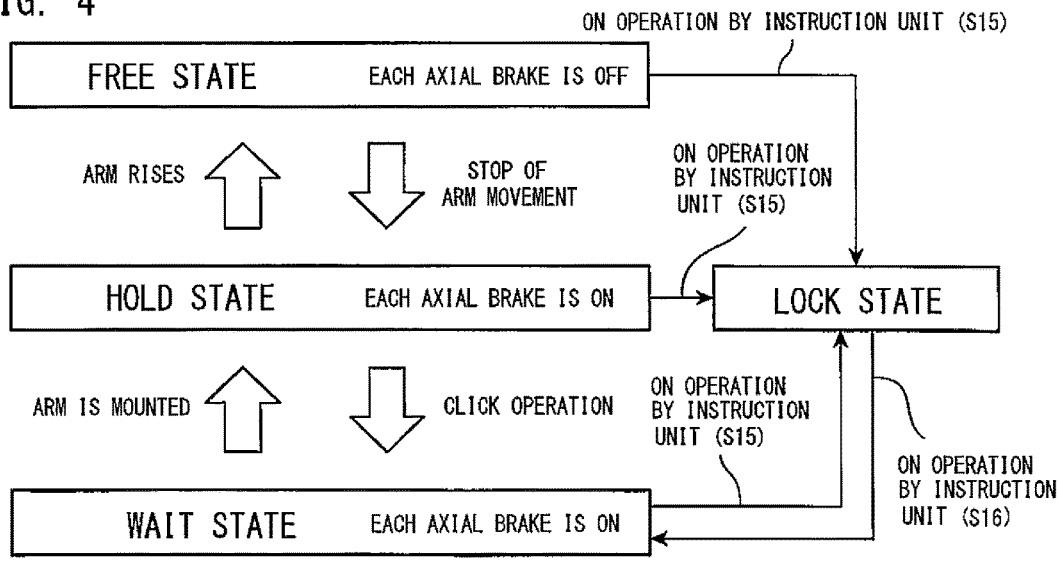
FIG. 4 is a state transition diagram schematically illustrating how the operating state of the body following support apparatus transitions in accordance with the state setting task illustrated in FIG. 3.

Next, the following describes a state setting task carried out by the computer 7, i.e. the CPU 71, with reference to FIGS. 3 and 4.

When the body following support apparatus 1 is powered on, the CPU 71 executes the state setting task in accordance with a program P1, which corresponds to the state setting task, stored in, for example, the ROM 72.

Specifically, when starting the state setting task, the CPU 71 sets the operation mode of the body following support apparatus 1 to the wait state in step S1. Specifically, the wait state is designed assuming that the forearm of the dominant arm of a doctor, referred to simply as a forearm, is not mounted on the arm holder 5.

For example, in step S1, the CPU 71 adjusts braking force of each of the brakes 31A, 32A, and 33A to completely brake the corresponding one of the joints 31, 32, and 33, thus completely fixing it. This operation will also be referred to as setting each axial brake to an on state. That is, because of the on state of each axial brake, the wait state causes the position of the arm holder 5 to be fixed even if the doctor removes the forearm from the arm holder 5. Note that, because no brakes are provided for the joints 34 and 35, the wait state enables both the direction around the rotational axis of the joint 34 of the arm holder 5, i.e. a vertical angle of the arm holder 5, and the direction around the rotational axis of the joint 35 of the arm holder 5, i.e. a horizontal angle of the arm holder 5, to be freely adjusted.

Next, the CPU 71 determines whether the forearm of a doctor is mounted on the arm holder 5 in accordance with at least one of the measurement signals sent from the encoders 31B to 33B and the force sensor 45.

For example, when downward force applied to the arm holder 5 has been equal to or higher than a predetermined level F1 that is equivalent to the weight of the forearm itself for at least a predetermined time T1, it is determined that the forearm of the doctor is mounted on the arm holder 5. Note that the threshold values F1 and T1 and the at least one measurement signal, which are referenced by the operation in step S3, can be selectively determined in accordance with a known algorithm described in, for example, patent document 1 set forth above. In particular, it is desired that the threshold level F1 and threshold time T1 and the at least one measurement signal are set to values depending on the type of a surgical operation for which the body following support apparatus 1 is used. This can be similarly applied to predetermined levels, predetermined times, and predetermined speeds described hereinafter.

The applicant of patent document 1 is the same as this application. The disclosure of patent document 1 is incorporated entirely herein by reference.

Upon determination that the forearm of a doctor is not mounted on the arm holder 5 (NO in step S3), the CPU 71 repeatedly performs the determination in step S3. Note that, in each of FIGS. 3 and 5, NO is abbreviated as "N".

Otherwise, upon determination that the forearm of a doctor is mounted on the arm holder 5 (YES in step S3), the state setting task proceeds to step S5. Note that, in each of FIGS. 3 and 5, YES is abbreviated as "Y".

In step S5, the CPU 71 sets the operating mode of the body following support apparatus 1 to the hold state; the hold state is designed assuming that a doctor holds the position of the arm holder 5, and tries to perform a surgical operation using the forearm mounted on the arm holder 5.

Specifically, the CPU 71 maintains the on state of each axial brake. Setting the hold state enables a doctor to move the forearm on the arm holder 5 whose position is fixed to thereby perform a fine surgical operation.

Following the operation in step S5, the CPU 71 determines whether the forearm mounted on the arm holder 5 moves, for example, rises, in accordance with at least one of the measurement signals sent from the encoders 31B to 33B and the force sensor 45 in step S7. For example, when downward force applied to the arm holder 5 has been maintained at zero for at least a predetermined time T2, it is determined that the forearm mounted on the arm holder rises In step S7, upon determination that the forearm mounted on the arm holder 5 does not rise (NO in step S7), the state setting task proceeds to step S9.

In step S9, the CPU 71 determines whether a click operation is carried out by the doctor in accordance with at least one of the measurement signals sent from the encoders 31B to 33B and the force sensor 45. Note that the click operation represents an operation of gently nudging the arm holder 5 downwardly with the doctor's forearm, i.e. an operation of gently pushing the arm holder 5 downwardly with the forearm.

For this reason, when downward force applied to the arm holder 5, which has increased to be equal to or more than a predetermined level F3, decreases to be equal to or less than the predetermined level F2 within a predetermined time T3, it is determined that a click operation has been carried out by the doctor. The predetermined level F3 represents that, when force applied to the arm holder 5 downwardly is equal to or more than the predetermined level F3, this force can be regarded as pressing force to the arm holder 5 based on the doctor's forearm.

Upon determination that the click operation is not carried out by the doctor (NO in step S9), the state setting task proceeds to step S7 set forth above.

Specifically, the determination of whether the forearm mounted on the arm holder 5 moves upwardly (step S7) and the determination of whether the click operation is carried out by the doctor's forearm (step S9) are repeatedly performed while the operating state of the body following support apparatus 1 is set to the hold state (step S5). Upon determination that the click operation is carried out by the doctor's forearm (YES in step S9) during execution of the loop including steps S7 and S9, the state setting task proceeds to step S1 set forth above. Then, the CPU 71 sets the operating state of the body following support apparatus 1 to the wait state in step S1.

Upon determination that the forearm mounted on the arm holder 5 rises (YES in step S7), the state setting task proceeds to step S11.

In step S11, the CPU 71 sets the operating state of the body following support apparatus 1 to the free state, which is an example of a release state. The free state is designed assuming that the doctor tries to make the arm holder 5 follow movement of the forearm mounted on the arm holder 5. Specifically, the CPU 71 turns off all the brakes 31A, 32A, and 33A corresponding to the joints 31, 32, and 33, thus releasing the braking of each of the joints 31, 32, and 33. This releasing will be referred to as setting each axial brake to an off state.

That is, because of the off state of each axial brake, the free state enables the arm holder 5 to follow doctor's movement of the forearm mounted on the arm holder 5. In addition, as described above, force applied from the arm holder 5 to the forearm mounted on the arm holder 5 is very weak, and slide resistance of each of the brakes is also small. For these reasons, the doctor is capable of causing the arm holder 5 to follow movement of the forearm without much force of the forearm.

Following the operation in step S11, the CPU 71 determines whether movement of the forearm mounted on the arm holder 5 has been stopped in accordance with at least one of the measurement signals sent from the encoders 31B to 33B and the force sensor 45 in step S13. For example, when the movement speed of the arm holder 5 has been maintained to be lower than a predetermined speed V1, which can be regarded as zero, for at least a predetermined time T4, it is determined that movement of the forearm mounted on the arm holder 5 has been stopped.

The movement speed of the arm holder 5 can be calculated based on the measurement signals of the respective encoders 31B, 32B, and 33B.

Upon determination that movement of the forearm mounted on the arm holder 5 has not been stopped (NO in step S13), the CPU 71 repeats the determination in step S13.

In contrast, upon determination that movement of the forearm mounted on the arm holder 5 has been stopped (YES in step S13), the state setting task proceeds to step S5, and the CPU 71 sets the operating state of the body following support apparatus 1 to the hold state in step S5, and thereafter performs the subsequent operations from step S7.

Executing the above state setting task by the computer 7 enables the operating state of the body following support apparatus 1 to transition as follows.

Referring to FIG. 4, when the body following support apparatus 1 is powered on, the operating state of the body following support apparatus 1 is set to the wait state (see step S1) with each axial brake being in the on state. When the forearm of a doctor is mounted on the arm holder 5 while the operating state of the body following support apparatus 1 is set to the wait state (YES in step S3), the operating state of the body following support apparatus 1 transitions from the wait state to the hold state (see step S5).

Even if the operating state of the body following support apparatus 1 transitions from the wait state to the hold state, each axial brake is maintained in the on state. When the forearm of the doctor mounted on the arm holder 5 rises while the operating state of the body following support apparatus 1 is set to the hold state (see YES in step S7), the operating state of the body following support apparatus 1 transitions from the hold state to the free state (see step S11).

While the operating state of the body following support apparatus 1 is set to the free state, each axial brake is in the off state, so that the doctor enables the arm holder 5 to follow movement of the forearm. When movement of the doctor's forearm mounted on the arm holder 5 is stopped while the operating state of the body following support apparatus 1 is set to the free state (see YES in step S13), the operating state of the body following support apparatus 1 transitions from the free state to the hold state (see step S5).

On the other hand, the doctor's click operation while the operating state of the body following support apparatus 1 is set to the hold state (see YES in step S9) enables the operating state of the body following support apparatus 1 to transition from the hold state to the wait state (see step S1).

Note that, as described above, the instruction device 90 is connected to the computer 7 as illustrated in FIG. 1. A doctor's turning on operation of the instruction unit 90 causes the CPU 71 to forcibly set the current operating state of the body following support apparatus 1, which is the wait state, the hold state, or the free state, to the lock state (see FIG. 4 and step S15). In the lock state, the CPU 71 maintains each axial brake in the on state independently of any force applied to the arm holder 5. When the instruction unit 90 is turned on by the doctor while the current operating state of the body following support apparatus 1 is set to the lock state, the CPU 71 forcibly set the operating state of the body following support apparatus 1 to the wait state (see step S16).

In the first embodiment, the free state is an example of the release state. Each of the wait state, the hold state, and the lock state is an example of a limit state. The springs 46 and 47 and the counterweights 48 are an example of a balance mechanism, and the encoders 31B, 32B, and 33B and the force sensor 45 are an example of detectors. The computer 7 is an example of a setting means, and the multijoint arm 3 is an example of a supporting member. The arm holder 5 is an example of a mount portion.

1-3 Advantageous Effect

Next, the following describes the following advantageous effects achieved by the body following support apparatus 1.

When a doctor rises the forearm mounted on the arm holder 5 to move the arm holder 5 to follow the forearm (see YES in step S7), the body following support apparatus 1 sets its operating mode to the free state (see step S11). This enables the arm holder 5 to follow movement of the forearm mounted on the arm holder 5. In addition, when the doctor stops movement of the forearm mounted on the arm holder 5 (see YES in step S13), the body following support apparatus 1 sets its operating state to the hold state (see step S5). This enables the arm holder 5 to be fixed to the stop position of the forearm mounted on the arm holder 5. This therefore achieves a first advantageous effect of enabling the doctor to smoothly perform a surgical operation with his or her forearm mounted on the arm holder 5 fixed to a desired position.

When the operating state of the body following support apparatus 1 is set to the hold state or the free state, the body following support apparatus 1 prevents its operating state from being set to the wait state corresponding to the state where the doctor's forearm is not mounted on the arm holder 5 unless the doctor's click operation or the doctor's turning on operation of the instruction device 90 is carried out.

The click operation or turning on operation of the instruction device 90 is a doctor's intentional operation. For this reason, the body following support apparatus 1 achieves a second advantageous effect of avoiding the possibility of the operating state of the body following support apparatus 1 being set to the wait state contrary to the doctor's intention. This improves the doctor's working efficiency, and relieves doctor's concerns about the body following support apparatus 1 being set to an operating state which is different from the doctor's intention.

In addition, because the click operation is a doctor's operation that applies force to the arm holder 5 in the upward direction in accordance with a predetermined pattern, the body following support apparatus 1 enables the doctor to perform the click operation with peace of mind.

The body following support apparatus 1 is capable of setting its operating state to the free state only when its operating state is set to the hold state. Specifically, while the operating state of the body following support apparatus 1 is set to the wait state, the body following support apparatus 1 prevents its operating state from being directly set to the free state.

That is, if the wait state corresponding to the state in which the doctor's forearm is not mounted on the arm holder 5 directly transitioned to the free state for moving the arm holder 5 follow movement of the forearm contrary to the doctor's intention, the doctor's working efficiency would be reduced.

From this viewpoint, the body following support apparatus 1 achieves a third advantageous effect of preventing the occurrence of drop in the doctor's working efficiency.

2. Second Embodiment 2-1 Operation

The structure of the body following support apparatus 1 according to the second embodiment is similar to the structure of the body following support apparatus 1 according to the first embodiment. A state setting task by the computer 7 according to the second embodiment is different from the state setting task according to the first embodiment in the following point.

Figure 5:
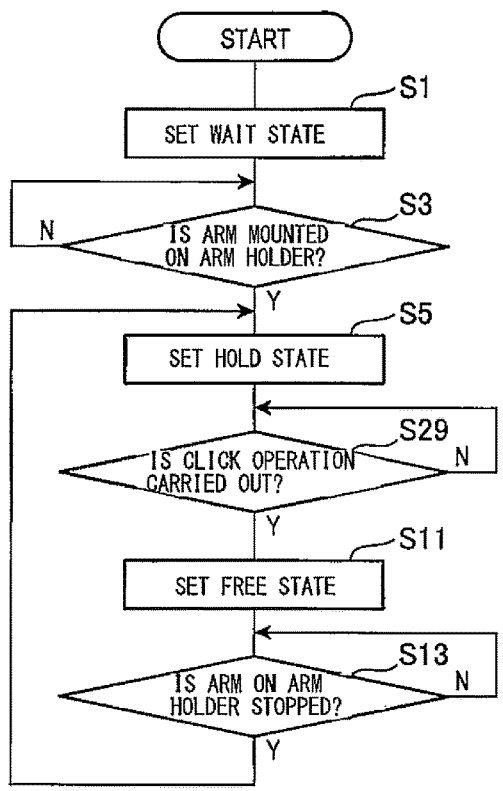
FIG. 5 is a flowchart schematically illustrating a state setting task in a body following support apparatus according to the second embodiment of the present disclosure.

The following describes the state setting task carried out by the computer 7 according to the second embodiment with reference to the flowchart illustrated in FIG. 5. The state setting task is carried out by the CPU 71 in accordance with a program P2, which corresponds to the state setting task, stored in, for example, the ROM 72. The program P2 is illustrated by a phantom line in the ROM 72 in FIG. 1. That is, the second embodiment is different in its state setting task from the first embodiment.

Thus, the body following support apparatus 1 according to the first embodiment or the second embodiment can store the programs P1 and P2 in, for example, the ROM 72. In this modification, the state setting task by the body following support apparatus 1 in accordance with the program P1 will be referred to as a first state setting task based on a first processing mode. In addition, the setting task by the body following support apparatus 1 in accordance with the program P2 will be referred to as a second state setting task based on a second processing mode.

Specifically, the CPU 71 according to this modification selectively executes the first state setting task based on the program P1 in response to a doctor's instruction indicative of selection of the first processing mode sent from the instruction device 90. In addition, the CPU 71 according to this modification selectively executes the first state setting task based on the program P2 in response to a doctor's instruction indicative of selection of the second processing mode sent from the instruction device 90.

The operations in steps S1 to S5 of the state setting task, i.e. the second state setting task, according to the second embodiment, are identical to those of the state setting task, i.e. the second state setting task, according to the first embodiment.

After setting the operating state of the body following support apparatus 1 to the hold state in step S5, the CPU 71 determines whether the click operation is carried out by the doctor in accordance with at least one of the measurement signals sent from the encoders 31B to 33B and the force sensor 45 in step S29.

Upon determination that the click operation has not been carried out by the doctor (NO in step S29), the CPU 71 repeatedly performs the determination in step S29.

Otherwise, upon determination that the click operation is carried out by the doctor (YES in step S29), the second setting task sequentially proceeds to steps S11 and S13 in the same manner as the first state setting task.

Specifically, when the click operation is carried out by the doctor (see YES in step S29), the CPU 71 sets the operating state of the body following support apparatus 1 to the free state in the same manner as the operation in step S11 of the first state setting task according to the first embodiment. Then, the CPU 71 repeatedly performs the determination in step S13 until movement of the doctors forearm mounted on the arm holder 5 is stopped (NO in step S13). In other words, the CPU 71 maintains the operating state of the body following support apparatus 1 in the free state until movement of the doctors forearm mounted on the arm holder 5 is stopped.

When movement of the doctor's forearm mounted on the arm holder 5 is stopped (YES in step S13), the second state setting task proceeds to step S5 in the same manner as the first state setting task. In step S5, the CPU 71 sets the operating mode of the body following support apparatus 1 to the hold state.

Executing the above second state setting task by the computer 7 enables the operating state of the body following support apparatus 1 to transition as follows.

Figure 6:
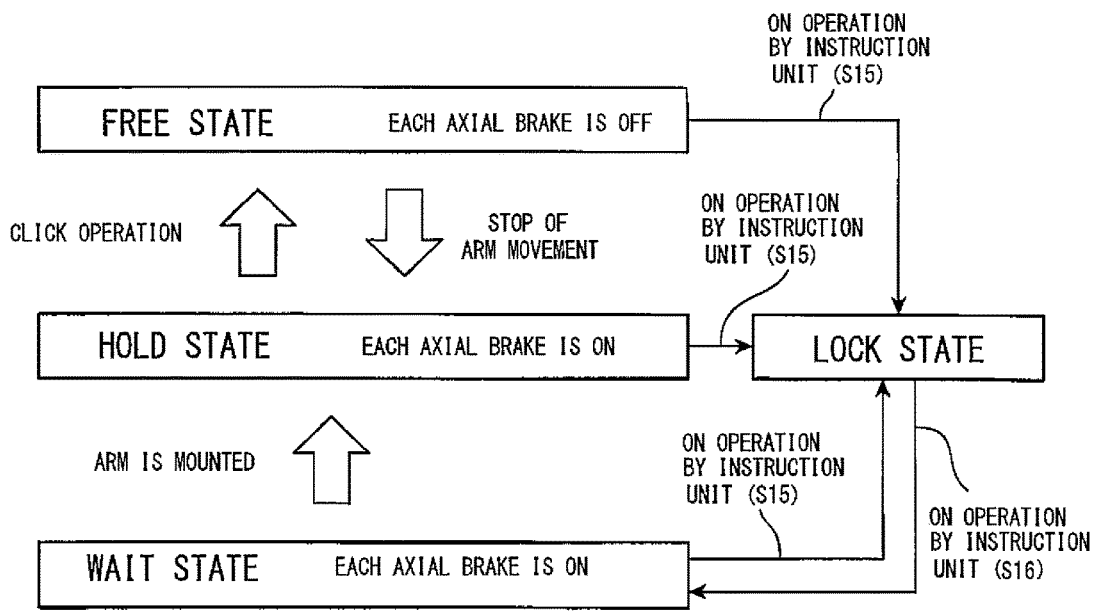
FIG. 6 is a state transition diagram schematically illustrating how the operating state of the body following support apparatus transitions in accordance with the state setting task illustrated in FIG. 5.

Specifically, referring to FIG. 6, when the body following support apparatus 1 is powered on, the operating state of the body following support apparatus 1 is set to the wait state (see step S1) with each axial brake being in the on state. When the forearm of a doctor is mounted on the arm holder 5 while the operating state of the body following support apparatus 1 is set to the wait state (YES in step S3), the operating state of the body following support apparatus 1 transitions from the wait state to the hold state (see step S5).

Even if the operating state of the body following support apparatus 1 transitions from the wait state to the hold state, each axial brake is maintained in the on state. When the forearm of the doctor mounted on the arm holder 5 performs the click operation (see YES in step S29), the operating state of the body following support apparatus 1 transitions from the hold state to the free state (see step S11).

While the operating state of the body following support apparatus 1 is set to the free state, each axial brake is in the off state, so that the doctor enables the arm holder 5 to follow movement of the forearm. When movement of the doctor's forearm mounted on the arm holder 5 is stopped while the operating state of the body following support apparatus 1 is set to the free state (see YES in step S13), the operating state of the body following support apparatus 1 transitions from the free state to the hold state (see step S5).

Note that, as described above, a doctor's turning on operation of the instruction unit 90 causes the CPU 71 to forcibly set the current operating state of the body following support apparatus 1, which is the wait state, the hold state, or the free state, to the lock state (see FIG. 4 and step S15). In the lock state, the CPU 71 maintains each axial brake in the on state independently of any force applied to the arm holder 5. When the instruction unit 90 is turned on by the doctor while the current operating state of the body following support apparatus 1 is set to the lock state, the CPU 71 forcibly set the operating state of the body following support apparatus 1 to the wait state (see step S16).

2-3 Advantageous Effect

The above body following support apparatus 1 according to the second embodiment achieves the third advantageous effect in the first embodiment as a first advantageous effect, and achieves the following advantageous effects.

When a doctor performs the click operation to move the arm holder 5 follow the forearm (see YES in step S29), the body following support apparatus 1 sets its operating mode to the free state (see step S11). This enables the arm holder 5 to follow movement of the forearm mounted on the arm holder 5. In addition, when the doctor stops movement of the forearm mounted on the arm holder 5 (see YES in step S13), the body following support apparatus 1 sets its operating state to the hold state (see step S5). This enables the arm holder 5 to be fixed to the stop position of the forearm mounted on the arm holder 5. This therefore achieves a second advantageous effect of enabling the doctor to smoothly perform a surgical operation with their forearm mounted on the arm holder 5 fixed to a desired position while intentionally performs click operations to move the arm holder 5.

The body following support apparatus 1 according to the second embodiment prevents its operating state from being set to the free state unless a doctor's click operation is carried out. For this reason, the body following support apparatus 1 achieves a third advantageous effect of avoiding the possibility of the operating state of the body following support apparatus 1 being set to the free state contrary to the doctor's intention. This improves the doctor's working efficiency, and relieves the doctor's concerns about the body following support apparatus 1 being set to an operating state which is different from the doctor's intention.

In addition, because the click operation is a doctor's operation that applies force to the arm holder 5 in the upward direction in accordance with the predetermined pattern, the body following support apparatus 1 enables the doctor to perform the click operation with peace of mind.

When the operating state of the body following support apparatus 1 according to the second embodiment is set to the hold state or the free state, the body following support apparatus 1 prevents its operating state from being set to the wait state corresponding to the state where the doctor's forearm is not mounted on the arm holder 5 unless the doctor's turning on operation of the instruction device 90 is carried out.

The turning on operation of the instruction device 90 is the doctor's intentional operation. For this reason, the body following support apparatus 1 according to the second embodiment achieves a fourth advantageous effect of avoiding the possibility of the operating state of the body following support apparatus 1 being set to the wait state contrary to the doctor's intention. This improves the doctor's working efficiency, and relieves doctor's concerns about the body following support apparatus 1 being set to an operating state which is different from the doctor's intention.

The body following support apparatus 1 according to the second embodiment necessitates a driver's intentional operation for switching the operating state of the body following support apparatus 1 from the hold state to the free state, or switching the operating state of the body following support apparatus 1 from the hold state to the wait state. For this reason, the body following support apparatus 1 according to the second embodiment achieves a fifth advantageous effect of stably maintaining the operating state of the body following support apparatus 1 in the hold state.

Specifically, the second state setting task of the body following support apparatus 1 according to the second embodiment is better suited for static surgeries having frequent opportunities for a doctor to fix the arm holder 5 to a predetermined position as compared with the first state setting task of the body following support apparatus 1 according to the first embodiment.

In contrast, the first state setting task of the body following support apparatus 1 according to the first embodiment is better suited for dynamic surgeries that necessitate a doctor to repeat the series of moving the arm holder 5 and stopping the movement of the arm holder 5 as compared with the second state setting task of the body following support apparatus 1 according to the second embodiment.

3. Modifications

The computer 7 according to each of the first and second embodiments adjusts braking force of each of the brakes 31A, 32A, and 33A to completely fix the corresponding one of the joints 31, 32, and 33, i.e. the multijoint arm 3, thus setting the operating state of the body following support apparatus 1 to the wait state or the hold state. The present invention is however not limited to the configuration.

For example, the computer 7 can adjust braking force of at least one of the brakes 31A, 32A, and 33A to enable a corresponding at least one of the joints 31, 32, and 33 to be slightly movable. The computer 7 according to each of the first and second embodiments performs control of braking force of each of the brakes 31A, 32A, and 33A in the wait state to be similar to control of braking force of a corresponding one of the brakes 31A, 32A, and 33A in the hold state. However, the computer 7 can perform control of braking force of each of the brakes 31A, 32A, and 33A in the wait state to be different from control of braking force of a corresponding one of the brakes 31A, 32A, and 33A in the hold state.

In each of the first and second embodiments, the springs 46 and 47 and the counterweights 48 constitute a balance mechanism that applies biasing force to the arm holder 5 while the operating state of the body following support apparatus 1 is set to the free state; this biasing-force application causes the arm holder 5 to follow movement of the forearm mounted on the arm holder 5. The present invention is however not limited to the configuration. For example, the balance mechanism can be configured to use plural counterbalances without using springs, can be comprised of only springs, or can be configured to use another known biasing-force applying means.

The computer 7 according to each embodiment variably sets the operating state of the body following support apparatus 1 in accordance with the measurement signals sent from the encoders 31B, 32B, and 33B and the force sensor 45 as detectors, but the present invention is not limited to the configuration.

For example, a sensor for measuring mounting of a doctor's forearm on the arm holder 5 based on change of a capacitance or based on interruption of a light path can be used. Specifically, contact sensors or proximity sensors can be used as detectors. In this modification, such a detector is capable of 1. Detecting the occurrence of a slight contact of a doctor's arm on the arm holder 5 and separation of the doctor's arm therefrom as the click operation or 2. Detecting the occurrence of a doctor's arm being close to the arm holder 5 and being separated therefrom as the click operation.

Each of the first and second state setting tasks according to the first and second embodiments includes an operation to determine whether the click operation is carried out, but the present invention is not limited to the configuration.

For example, the computer 7 can determine whether the operating state of the body following support apparatus 1 is set to the free state using one of known methods disclosed in patent document 1 in step S7 or S29.

For example, as disclosed in patent document 1, when it is determined that instruction information based on doctor's operations of a foot switch as an example of the instruction device 90 is sent to the computer 7 from the foot switch as the operation in step S7 or S29, the computer 7 can set the operating state of the body following support apparatus 1 to the free state in step S11.

In addition, as disclosed in patent document 1, when it is determined that force applied to the arm holder 5 has been equal to or larger than 1.5 kgf (14.7 N) for 100 milliseconds (ms) as the operation in step S7 or S29, the computer 7 can set the operating state of the body following support apparatus 1 to the free state in step S11.

In step S7 or S20 according to each of the first and second embodiments, the operation that determines whether the operating state of the body following support apparatus 1 is set to the free state using one of known methods disclosed in patent document 1 prevents the operating state of the body following support apparatus 1 from directly transitioning from the wait state to the free state. This modification therefore achieves the third advantageous effect achieved by the first embodiment.

The body following support apparatus 1 according to each of the first and second embodiments is configured to prevent its operating state from directly transitioning from one of the wait state and the free state to the other thereof, but the present invention is not limited to the configuration.

For example, the computer 7 of the body following support apparatus 1 according to each of the first and second embodiments can be configured to cause the operating state of the body following support apparatus 1 to directly transition from the free state to the wait state upon determination that the rising speed of the doctor's forearm mounted on the arm holder 5 is higher than a predetermined threshold speed (YES in step S12 illustrated by a phantom line in FIG. 3). Note that, upon determination that the rising speed of the doctor's forearm mounted on the arm holder 5 is equal to or lower than the predetermined threshold speed (NO in step S12), the computer 7 performs the operation in step S13.

Note that the rising speed of the doctor's forearm mounted on the arm holder 5 can be regarded as the rate of change, i.e. the time differential, of downward force applied to the arm holder 5. That is, when the rate of change of the downward force applied to the arm holder 5 is lower than a predetermined threshold level, it can be determined that the rising speed of the doctor's forearm mounted on the arm holder 5 is higher than the predetermined threshold speed. Note that this predetermined threshold level can be obtained by subtracting a predetermined positive level from the predetermined level set forth above. In this modification, it is possible to improve the safety of the body following support apparatus 1.

In addition, the computer 7 can determine whether the click operation is carried out by the doctor in accordance with at least one of the measurement signals sent from the encoders 31B to 33B and the force sensor 45 (see step S4 illustrated by a phantom line in FIG. 3). Upon determination that the click operation is carried out (YES in step S4), the computer 7 can be configured to directly switch the operating state of the body following support apparatus 1 from the wait state to the free state in step S11. Note that upon determination that the click operation is not carried out (NO in step S4), the computer 7 can be configured to perform the operation in step S5.

In each of the first and second embodiments, the click operation is defined as an operation of gently nudging the arm holder 5 downwardly with the doctor's forearm, i.e. an operation of gently pushing the arm holder 5 downwardly with the forearm, but the present invention is not limited thereto.

For example, the click operation san be defined as a series of

1. Temporarily raising the arm mounted on the arm holder by the doctor
2. Pressing the arm holder 5 downwardly by the doctor
3. Raising the arm again immediately after the pressing by the doctor The click operation can also be defined as two sets of
1. Pressing the arm holder 5 downwardly by the doctor
2. Raising the arm immediately after the pressing by the doctor The two sets of pressing the arm holder 5 downwardly and raising the arm immediately after the pressing by the doctor will be referred to as a double click operation.

The click operation can further be defined as a series of
1. Moving the arm mounted on the arm holder 5 in the right direction, left direction, or elbow-side direction from the doctor
2. Raising the arm by the doctor immediately after the movement of the arm The body following support apparatus 1 according to each of the first and second embodiments includes, as the operating state, the hold state and wait state each serving as an example of the limit state, but the present invention is not limited thereto. For example, the body following support apparatus 1 according to the second embodiment can include only the hold state as the limit state without including the wait state as the limit state. In this modification, the body following support apparatus 1 includes two types of its operating state including the hold state and free state except for the lock state; the lock state is set by doctor's instructions sent from the instruction device 90. This results in the operations of the body following support apparatus 1 being simplified.

The functions of one element in each of the first and second embodiments can be distributed as plural elements, and the functions that plural elements have can be combined into one element. At least part of the structure of each of the first and second embodiments can be replaced with a known structure having the same function as the at least part of the structure of the corresponding embodiment. A part of the structure of each of the first and second embodiments can be eliminated. At least part of the structure of one of the first and second embodiments can be added to or replaced with the structure of the other of the first and second embodiments. All aspects included in the technological ideas specified by the language employed by the claims constitute embodiments of the present invention.

The present invention can be implemented by various embodiments in addition to the body following support apparatuses; the various embodiments include systems each including one of the above body following support apparatuses, programs for making a computer serve as a setting means in each of the body following support apparatuses, storage media storing the programs, and setting methods for the body following support apparatuses.

This application is based on and claims the benefit of priority from Japanese Patent Application No. 2015-066722, the disclosure of which is incorporated in its entirety herein by reference.

REFERENCE SINS LIST

1 Body following support apparatus
3 Multijoint arm
5 Arm holder
7 Computer
31, 32, 33, 34, 35 Joint
31A, 32A, 33A Brake
31B, 32B, 33B Encoder
45 Force sensor
46, 47 Spring
48 Counterweight
90 Instruction device

The invention claimed is:
1. A body following support apparatus for supporting a part of a body of an operator, the apparatus comprising:
  a mount portion on which the part of the body of the operator is mountable;
  a support member that has at least one joint and supports the mount portion to be movable at least vertically by bending of the at least one joint;
  a brake for achieving:
    a limit state as an operating state of the body following the apparatus, the limit state limiting a function of the at least one joint of the support member to limit movement of the mount portion; and
    a release state as the operating state of the body following the apparatus, the release state releasing the limit of the function of the at least one joint to release the limit of the movement of the mount portion;
  a balance mechanism that applies upward biasing force to the mount portion in the release state to cause the mount portion to follow movement of the part of the body mounted on the mount portion;
  a detector that detects, while the part of the body is mounted on the mount portion, at least one of:
    force applied from the part of the body to at least one of the mount portion and a fixing member;
    torque applied from the part of the body to the mount portion;
    an acceleration of the mount portion;
    a speed of the mount portion;
    a position of the mount portion;
    a contact state between the mount portion and the part of the body; and a state of the part of the body being close to the mount portion; and a setting means configured to control the brake to set the operating state of the body following apparatus to any one of the limit state and the release state in accordance with:
a detection result of the detector;
a result of whether a click operation is carried out with the part of the body,
the click operation being defined as an intentional movement of the part of the body by the operator in accordance with a predetermined pattern;
wherein the click operation is defined as an operator's operation to:
press the mount portion in a predetermined direction other than an upward direction with the part of the body by the operator; and
stop the pressing immediately after the pressing.

2. The body following support apparatus according to claim 1, wherein:
the limit state includes:
a hold state corresponding to a state in which the part of the body is mounted; and
a wait state corresponding to a state in which the part of the body is not mounted; and
the setting means is configured to set the operating state of the body following support apparatus to the wait state upon determination that the click operation is carried out with the hold state being set to the operating state of the body following support apparatus.

3. The body following support apparatus according to claim 1, wherein:
the setting means is configured to set the operating state of the body following support apparatus to the release state upon determination that the click operation is carried out with the limit state being set to the operating state of the body following support apparatus.

4. The body following support apparatus according to claim 1, wherein:
the setting task is configured to:
set the operating state of the body following support apparatus to the limit state upon determination that the mount portion has been stopped for a predetermined time with the release state being set to the operating state of the body following support apparatus.

5. The body following apparatus according to claim 1, wherein the part of the body mounted on the mount portion is an arm.

6. A body following support apparatus for supporting a part of a body of an operator, comprising:
a mount portion on which the part of the body of the operator is mountable;
a support member that has at least one joint and supports the mount portion to be movable at least vertically by bending of the at least one joint;
a brake for achieving:
a limit state as an operating state of the body following support apparatus, the limit state limiting a function of the at least one joint of the support member to limit movement of the mount portion; and
a release state as the operating state of the body following support apparatus, the release state releasing the limit of the function of the at least one joint to release the limit of the movement of the mount portion;
a balance mechanism that applies upward biasing force to the mount portion in the release state to cause the mount portion to follow movement of the part of the body mounted on the mount portion;

a detector that detects, while the part of the body is mounted on the mount portion, at least one of:
force applied from the part of the body to at least one of the mount portion and the fixing member;
torque applied from the part of the body to the mount portion;
an acceleration of the mount portion;
a speed of the mount portion;
a position of the mount portion;
a contact state between the mount portion and the part of the body; and
a state of the part of the body being close to the mount portion; and a setting means configured to control the brake to set the operating state of the body following support apparatus to any one of the limit state and the release state,
the limit state including:
a hold state corresponding to a state in which the part of the body is mounted on the mount portion; and
a wait state corresponding to a state in which the part of the body is not mounted on the mount portion; and
the setting means being configured to:
perform, based on a detection result of the detector, at least one of:
a first switching task to switch the operating state of the body following support apparatus from the release state to the hold state;
a second switching task to switch the operating state of the body following support apparatus from the hold state to the release state;
a third switching task to switch the operating state of the body following support apparatus from the wait state to the hold state;
a fourth switching task to switch the operating state of the body following support apparatus from the hold state to the wait state; and
a fifth switching task to switch the operating state of the body following support apparatus from the release state to the wait state; and
prevent the operating state of the body following support apparatus from being directly switched from the wait state to the release state;
wherein a setting task is configured to:
determine, based on the detection result of the detector, whether a click operation is carried out with the part of the body, the click operation being defined as an intentional movement of the part of the body by the operator in accordance with a predetermined pattern; and
determine whether to perform at least one of the first to fifth switching tasks in accordance with a result of the determination of whether the click operation is carried out;
and wherein:
the click operation is defined as an operator's operation to:
press the mount portion in a predetermined direction other than an upside direction with the part of the body; and
stop the pressing immediately after the pressing.

7. The body following support apparatus according to claim 6, wherein the setting means is configured to set the operating state of the body following support apparatus to the release state upon the detection result of the detector representing a state in which the part of the body mounted on the arm holder rises with the operating state of the body-follow-up device being set to the hold state.

* * * * *